(12) United States Patent
Kang et al.

(10) Patent No.: US 8,389,965 B2
(45) Date of Patent: Mar. 5, 2013

(54) METHOD AND DEVICE OF IRRADIATION OF LOGS WITH ELECTRON BEAMS AS A PHYTOSANITARY TREATMENT

(75) Inventors: Kejun Kang, Beijing (CN); Haifeng Hu, Beijing (CN); Chuanxiang Tang, Beijing (CN); Yuanjing Li, Beijing (CN); Qitian Miao, Beijing (CN); Huayi Zhang, Beijing (CN); Junli Li, Beijing (CN); Zhiqiang Chen, Beijing (CN); Ming Hu, Beijing (CN); Ming Huang, Beijing (CN); Yaohong Liu, Beijing (CN); Wanlong Wu, Beijing (CN); Hui Zhang, Beijing (CN); Shenjin Ming, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 349 days.

(21) Appl. No.: 12/101,687

(22) Filed: Apr. 11, 2008

(65) Prior Publication Data
US 2008/0251156 A1 Oct. 16, 2008

(30) Foreign Application Priority Data
Apr. 12, 2007 (CN) .......................... 2007 1 0065382

(51) Int. Cl.
*G01N 23/00* (2006.01)
*H01J 37/20* (2006.01)
(52) U.S. Cl. ............ 250/492.3; 250/453.11; 250/454.11; 250/455.11; 378/64; 378/65; 378/68; 378/69; 144/4.2; 144/335
(58) Field of Classification Search .............. 250/455.11, 250/453.11, 454.11, 492.3, 492.1; 378/64, 378/65, 68, 69; 144/4.2, 335
See application file for complete search history.

(56) References Cited

U.S. PATENT DOCUMENTS

| 6,833,551 B2 * | 12/2004 | Avnery | 250/492.3 |
| 2003/0201401 A1 * | 10/2003 | Rose | 250/492.1 |
| 2004/0113094 A1 * | 6/2004 | Lyons et al. | 250/435 |

FOREIGN PATENT DOCUMENTS

| DE | 201 17 364 | 3/2002 |
| DE | 10 2006 035 087 | 2/2007 |
| JP | 50-7123 | 3/1975 |
| SU | 1188064 | 10/1985 |
| WO | WO 01/62339 | 8/2001 |
| WO | WO 02/075747 | 9/2002 |

* cited by examiner

*Primary Examiner* — Jack Berman
*Assistant Examiner* — Meenakshi S Sahu
(74) *Attorney, Agent, or Firm* — Kenyon & Kenyon LLP

(57) ABSTRACT

For quarantine treatment of a farming and forestry product for pest control, a method and a device may irradiate logs as a phytosanitary treatment with electron beams. The method may include: spreading the logs; aligning the spread logs to be flush at one end; conveying the spread and flush logs laterally; conveying the logs longitudinally through an irradiation field formed by accelerators to provide treatment of irradiation with the electron beams; throwing the irradiated logs out; and laterally conveying the logs away. The device may include a conveying device for conveying the logs, a shielding structure surrounding the conveying device, and accelerators provided in the conveying path of the conveying device. Two or more accelerators may be provided in centrosymmetry about the conveying path.

27 Claims, 6 Drawing Sheets

METHOD AND DEVICE OF IRRADIATION OF LOGS WITH ELECTRON BEAMS AS A PHYTOSANITARY TREATMENT

FIELD OF THE INVENTION

The present invention relates to a technical field of the quarantine treatment of a farming and forestry product for pest control, particularly, to a method and a device of irradiation of logs with electron beams as a phytosanitary treatment.

BACKGROUND INFORMATION

With rapid development of farming and forestry, it is seriously desired to strengthen the inspection and quarantine of the imported logs and wood products to prevent spread of risky pests. Conventional quarantine treatment of the logs employs a method of fumigation by Methyl Bromide. This method has distinct shortcomings and limitations. Methyl Bromide would deplete the ozone layer of the atmosphere, and according to the amendment to "The Montreal Protocol on Substances that Deplete the Ozone Layer" at Copenhagen (1992), in order to protect the ozone layer of the atmosphere, each developed country of the parties of the Protocol shall ensure that for the twelve-month period commencing on Jan. 1, 2005 and in each twelve-month period thereafter, its calculated level of consumption of Methyl Bromide does not exceed zero, and, each developing country shall ensure that for the twelve-month period commencing on Jan. 1, 2015 and in each twelve-month period thereafter, its calculated level of consumption of Methyl Bromide does not exceed zero. Fumigation by Methyl Bromide is infeasible at a temperature below 5° C. Methyl Bromide is poisonous to nerve, and would be released to the atmosphere after the treatment of fumigation, contaminating the living environment of human being. Further, phytosanitary treatment by fumigation with Methyl Bromide is fairly inefficient because it needs over 16 hours to seal the logs to complete one treatment. Additionally, at some ports, particularly the ports of maritime transportation, the logs will be directly processed after being loaded onto the ground. Therefore it is infeasible to conduct the conventional quarantine treatment at the harbor districts with limited area.

SUMMARY OF THE INVENTION

Embodiments of the present invention provide a method and a device which solve the above disadvantages. Embodiments of the present invention provide for a highly efficient quarantine treatment and strikes a good balance between safety and efficiency. The system and method provide for irradiation of logs with electron beams as a phytosanitary treatment. The system and method employ a plurality of linear accelerators (LINACs) to generate electron beams for conducting irradiation treatment of logs, having the minimum absorbed dose at a certain depth from the log surface to meet the standard of quarantine requirement, resulting in sterility or death of the pests living commensally adjacent to the bark of the log, and thus achieving the purpose of phytosanitary treatment of the logs.

The present invention provides a method of conducting irradiation of logs with electron beams as a phytosanitary treatment. The method includes steps of: spreading the logs; aligning the spreaded logs to be flush at one end; conveying the spreaded and aligned logs laterally and then longitudinally; conveying the logs through an irradiation field formed by accelerators during the conveying of the logs in the longitudinal direction, to implement irradiation treatment with electron beams; and throwing the irradiated logs out and laterally conveying the logs away.

According to a preferred embodiment of the present invention: during the process of spreading and aligning, the conveying direction of the logs is perpendicular to the axis of the logs; when the lateral conveying is changed to longitudinal conveying, the conveying direction of the log is changed by 90°, such that the conveying direction is consistent with the axis of the logs during the longitudinal conveying; and, during the process of throwing and laterally conveying the logs away, the conveying direction of the logs is changed by 90° once again.

According to a exemplary embodiments of the present invention, during a conveying process of the logs, the two lateral conveying processes can be conducted at the same side or different sides of the longitudinal conveying process.

The present invention provides a device for conducting irradiation of logs with electron beams as a phytosanitary treatment, including a conveying device for conveying the logs, a shielding structure surrounding the conveying device, and accelerators provided in the conveying path of the conveying device, two of which accelerators are provided in centrosymmetry about the conveying path.

According to a preferred embodiment of the present invention, there exists two accelerators. One of the accelerators is arranged above the conveying device and the other of the accelerators is arranged below the conveying device.

According to a preferred embodiment of the present invention, there exists three accelerators. One of the accelerators is arranged above the conveying device. The other two of the accelerators are arranged below the conveying device at, respectively, the left and right thereof.

According to a preferred embodiment of the present invention, a scanning box is mounted at an end of the accelerator, a deflecting magnet is mounted on the scanning box at a position adjacent to an exit titanium window, such that the electron beams introduced out of the scanning box are deflected into parallel beams perpendicular to the conveying plane to irradiate the logs.

According to a preferred embodiment of the present invention, a protective device is mounted above the accelerator below the conveying device to prevent damage of the accelerator caused by the sundries from the conveying device.

According to a preferred embodiment of the present invention, the conveying device includes a loading device, a longitudinal conveying device, and an unloading device. The loading device makes the logs spread and flush, and then conveys the logs to the longitudinal conveying device; the longitudinal conveying device conveys the logs through a irradiation field formed by accelerators as a quarantine treatment; and the unloading device conveys the irradiated logs out of the processing.

According to a preferred embodiment of the present invention, the loading device includes a log spreading mechanism, an end aligning mechanism, a loading mechanism, and a lateral loading conveying mechanism; the longitudinal conveying device includes a longitudinal conveying mechanism; and the unloading device includes a log throwing mechanism and a lateral unloading conveying mechanism; wherein the longitudinal conveying mechanism is divided into two portions, between which there exists a spatial distance to ensure the electron beams introduced out of the accelerators can irradiate the logs directly without irradiating the conveying mechanism.

According to a preferred embodiment of the present invention, the lateral loading conveying mechanism is a scraper conveyor which operates continuously, the distance between the scrapers and the operation speed are adjusted to ensure the logs can be intermittently loaded into the longitudinal conveying mechanism, and to ensure the time interval between two logs entering the longitudinal conveying mechanism.

According to a preferred embodiment of the present invention, the conveying direction is changed by 90° from the lateral loading conveying mechanism to the longitudinal conveying mechanism, and the conveying direction is changed by 90° from the longitudinal conveying mechanism to the lateral unloading conveying mechanism, while the lateral loading conveying mechanism and the lateral unloading conveying mechanism are at certain angles with respect to the horizon plane, thereby reducing leakage of the radiation.

According to a preferred embodiment of the present invention, the lateral loading conveying mechanism and the lateral unloading conveying mechanism can be mounted at the same side or different sides of the longitudinal conveying device According to a preferred embodiment of the present invention, a set of conveying devices can be provided with a plurality of loading devices, longitudinal conveying devices, and unloading devices to make a plurality of conveying lines to operate simultaneously.

According to a preferred embodiment of the present invention, one longitudinal conveying device can connect to one or more loading devices and one or more unloading devices to match the loading and unloading speeds with the longitudinal conveying speed.

According to a preferred embodiment of the present invention, the shielding structure includes: shielding walls surrounding the conveying device, two throat plates, and a maze for access by operators, wherein the throat plates are located between the loading entrance and the electron source and between the electron source and the unloading exit.

According to a preferred embodiment of the present invention, the shielding walls are provided with a certain number of buttresses to lower the radiation level outside the loading entrance and outside the unloading exit caused by the scattered X-rays, which are the secondary radiation generated by the primary electron beams hitting on the logs and the scattered electrons hitting on the conveying device.

According to a preferred embodiment of the present invention, the accelerators are staggered along the longitudinal conveying direction of the conveying device.

According to a preferred embodiment of the present invention, energy of the accelerators in use is selected from a range of 10-14 MeV.

The present invention can provide following advantages.

The present invention uses the irradiation with electron beams to exert biologic effects on the pests adjacent to the bark of the logs directly or indirectly, achieving the quarantine purpose by making the pests in the logs being sterile or unable to develop to an adult, or even killing the pests. Compared to the conventional technique, the quarantine treatment of the present invention is more effective, safe, pollution free, easy to use, and conveniently manipulated. Further the quarantine treatment is not limited by environmental temperature.

Additionally, the present invention employs a set of automatic conveying devices which contain a plurality of independent and non-interferential conveying lines and is suitable for use with the quarantine irradiation system for logs with electron beams according to the present invention, and further employs shielding walls with buttresses, throat plates, and a conveying structure capable of changing the conveying directions to provide radiation protection for the system, thereby enhancing the reliability of the system, facilitating radiation shielding of electrons, and easy for implementing and the maintenance.

DETAILED DESCRIPTION

The present invention will be described according to exemplified embodiments thereof. However, the invention is not limited thereto.

In an example embodiment of the present invention electron beams may be used in a cost-effective and feasible way to conduct irradiation as a quarantine treatment to logs. In particular, such use takes into consideration factors such as that the cost will be too high to conduct irradiation of the logs of the non-whole vehicle, which are processed after landing, with X-ray as a quarantine treatment due to the penetrating characteristic of X-ray in mass and that most of the pests in the logs live commensally adjacent to the bark of the logs.

According to a preferred embodiment of the present invention, two or three accelerators can be used to generate irradiation field with electron beams, a set of automatic conveying devices with several conveying lines independent and un-interferential with each other is used to convey the logs through the irradiation field to conduct the irradiation as a phytosanitary treatment, making the minimum absorbed dose at a certain depth from the log surface to meet the standard of quarantine requirement.

Figure 1:
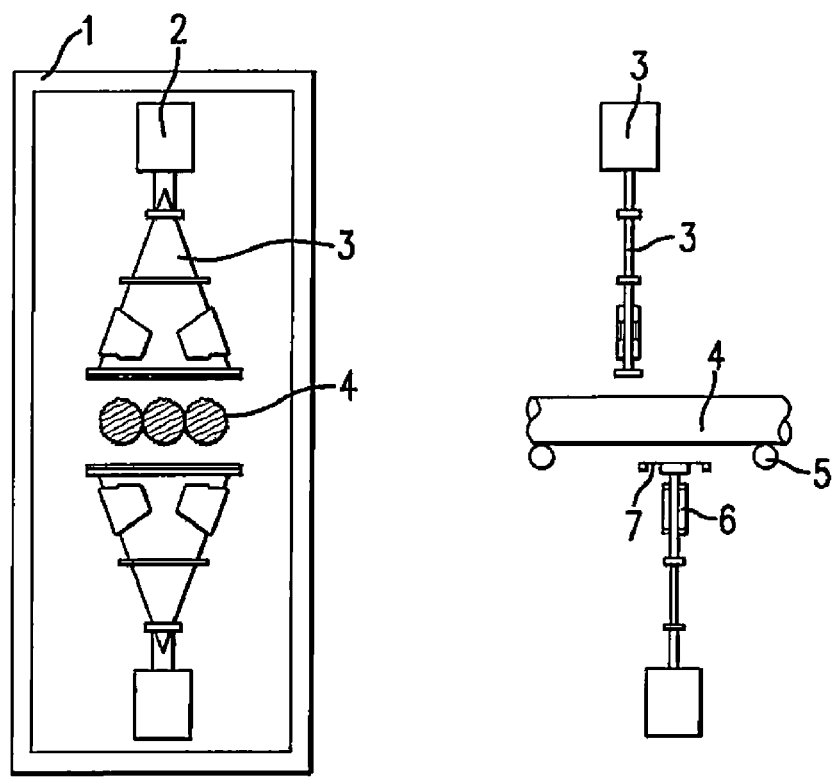
FIG. 1 is a view of the structural principle of the configuration of the device according to an example embodiment of the present invention.

FIG. 1 shows the structural principle of the device of the invention. As shown in FIG. 1, the device for conducting irradiation treatment of the logs 4 with the electron beams according to the present invention may include a shielding structure 1, accelerators 2 (each including a scanning box 3 and may include a deflecting magnet 6), a conveying device 5, and a protective device 7. The accelerators 2, conveying device 5, and protective device 7 are provided in the shielding structure 1, wherein two accelerators 2 can be arranged above and below the conveying device 5 respectively. The conveying device 5 can convey one or more logs in a row through the irradiation field formed by the accelerators 2.

Differing from X-ray, electron has a maximum range in the mass. Therefore using one accelerator cannot obtain a good effect of irradiation as a quarantine treatment. Therefore, the preferred embodiment of the present invention employs a scheme of irradiating a plurality of logs in one row simultaneously by using two accelerators as stated above. The two accelerators can be arranged symmetrically on the left and right, or can be arranged up and down, etc. Although the left-right arrangement is relatively simple compared to the up-down arrangement, the left-right arrangement brings a big problem in conveying the plurality of logs in one row, the present invention therefore employs the up-down arrangement in the preferred embodiment.

Additionally, the maximum ranges in the log of electrons with different energies are different, while the maximum range in the log of electron influences the effect of the quarantine treatment directly. Normally, the energy of electron is higher, and maximum range in the log will be longer, which results in a better effect of irradiation as a quarantine treatment, in case that all the other conditions are the same. However, if the energy is too high, serious induced radioactivity will be generated. Therefore, the inventor, upon calculation, found that the electron beam with the energy ranging from 10 to 14 MeV is suitable for irradiation as a quarantine treatment of the log. Therefore, according to the preferred embodiment of the present invention, the accelerators with energy ranging from 10 to 14 MeV are selected to ensure the induced radioactivity generated will not harm the operator and public.

It should be noted that, the accelerator used by the present invention is an electrical device which will not pollute the atmosphere and the environment, the application of which is not influenced by the environmental temperature, and as long as the power supply meets the requirement, application of the invention is feasible. The accelerator only generates electron beams during operation, and will not generate electron beams after being turned off. Therefore, there exists no problem of waste treatment which would otherwise result in the case of using a radioisotope source.

The scanning box 3 is mounted at the end of the accelerator. A deflecting magnet 6 can be mounted on the scanning box 3 adjacent to the exit of the titanium window, such that the electron beams introduced from the scanning box can be deflected into parallel beams which are perpendicular to the plane of the conveying line to irradiate the logs. Therefore, the problem that in different conveying lines the distribution of absorbed doses is different in the logs can be solved.

Figure 2:
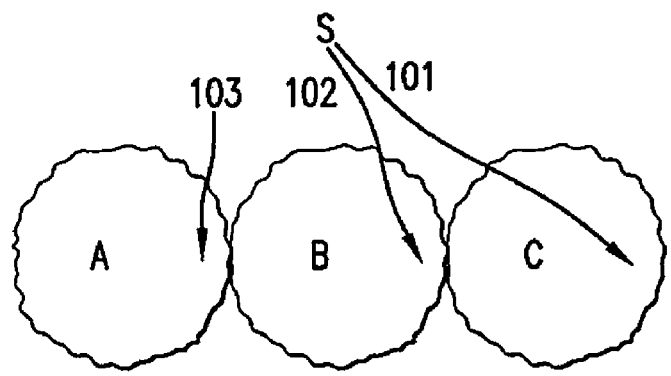
FIG. 2 is an illustration showing the influences to the absorbed doses by the emanative beams and the parallel beams at the corresponding positions inside different logs in a same row, according to an example embodiment of the present invention.

FIG. 2 is an illustration showing the influences to the absorbed doses by the emanative beams and the parallel beams at the corresponding positions inside logs in different conveying lines in a same row. As shown in FIG. 2, the electron beams 101 and 102 are electron beams emitted from a same point S. Because the incidence angles into the logs B and C are different, the electron beams 101 and 102 are different in terms of distance of penetration for reaching the corresponding positions in the logs B and C, resulting in the distributions of absorbed doses in the logs B and C being different. Therefore, when the dose at a position inside the log C which is further from the source point S meets the standard of quarantine requirement, the dose at the corresponding position inside the log B which is closer to the source point S will go far beyond the quarantine requirement, resulting in waste of power. However, if the deflecting magnet is used to change the emanative beams with a certain emanative angle into the parallel beams perpendicular to the plane of the conveying line, similar to electron beam 103, the absorbed dose distributions inside the logs A, B, and C can keep substantially the same, saving the cost accordingly.

Additionally, in the preferred embodiment of the present invention, to protect the accelerator under the conveying device, a protective device 7 is further provided. The protective device 7 is mounted above the scanning box of the lower accelerator for protecting the lower accelerator from damage caused by the bark, dust, and sundries falling from the logs on the conveying device.

Figure 3:
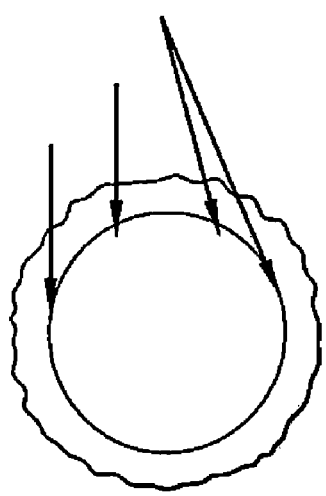
FIG. 3 is an illustration showing the different distances that the electron beams travel through in different directions when reaching the same depth from the surface of the log.
Figure 4:
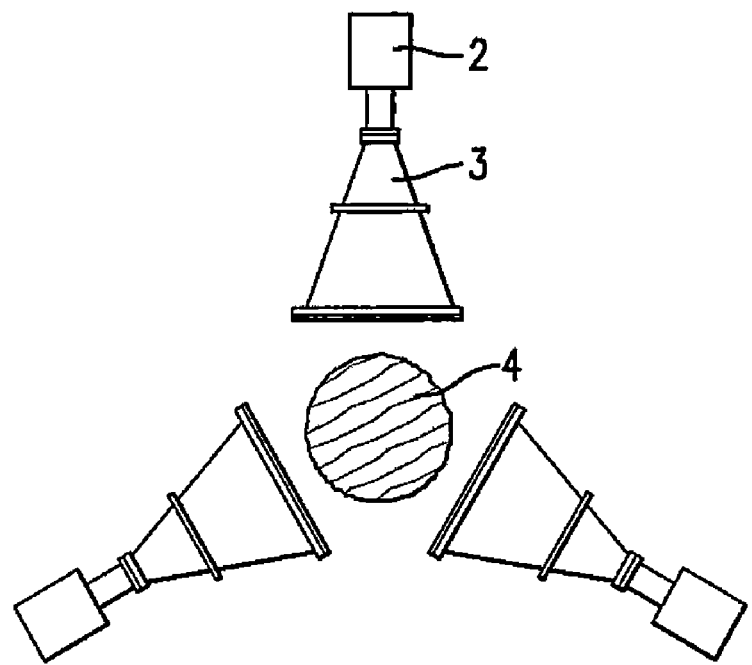
FIG. 4 is an illustration showing the layout of the three accelerators according to an example embodiment of the present invention.
Figure 5:
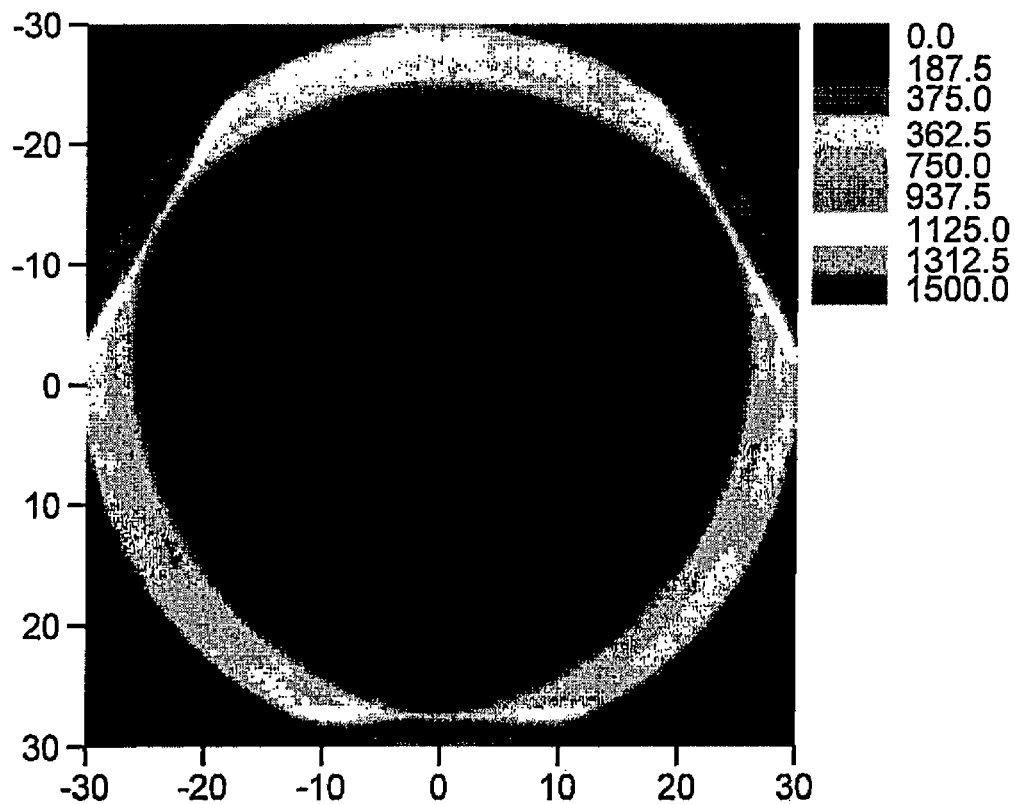
FIG. 5 is an illustration showing the absorbed dose distribution inside the log when three accelerators are employed for irradiation according to an example embodiment of the present invention.

Irrespective of the emanative beams or parallel beams, when the electrons reach, along different paths, the different positions at the same depth from the surface of the same log, the penetrating distances are different (referring to FIG. 3). Therefore, when the diameter of the log to be treated is relatively large, because the electron has the maximum range in the log, a portion adjacent to the bark of the log will not be irradiated at all. Therefore, according to the preferred embodiment of the present invention, in the case that the log 4 has a relatively large diameter, to attain a good effect of quarantine treatment, three accelerators 2 can be symmetrically arranged around the log as shown in FIG. 4 to conduct symmetrical irradiation. This scheme can only deal with one log in one cycle. FIG. 5 is an illustration showing the absorbed dose distribution in the same log under irradiation by three accelerators, which shows visually the effect of irradiation. Additionally, in the case that the log has an even larger diameter, additional accelerators can be further added to attain a good effect of quarantine treatment. Except for three fusiform hatched portions which bear relatively more irradiation, the other portions at the surface of the log are irradiated generally even and appropriate.

Additionally, to avoid damage of the device caused by irradiation between the accelerators, the accelerators can be staggered from each other along the conveying direction of the logs when providing the accelerators.

In terms of conveying the logs, the present invention employs log spreading mechanism(s), end aligning mechanism(s), loading mechanism(s), lateral loading conveying mechanism(s), longitudinal conveying mechanism(s), log throwing mechanism(s), and lateral unloading conveying mechanism(s) which are commonly used in the forestry operation to constitute a set of conveying devices 5 which contains a plurality of independent and un-interferential conveying lines and is suitable for use with the irradiation system as a quarantine treatment for the logs with electron beams according to the present invention. Therefore, the reliability of the system is enhanced and the radiation protection and the system maintenance is facilitated.

Figure 6:
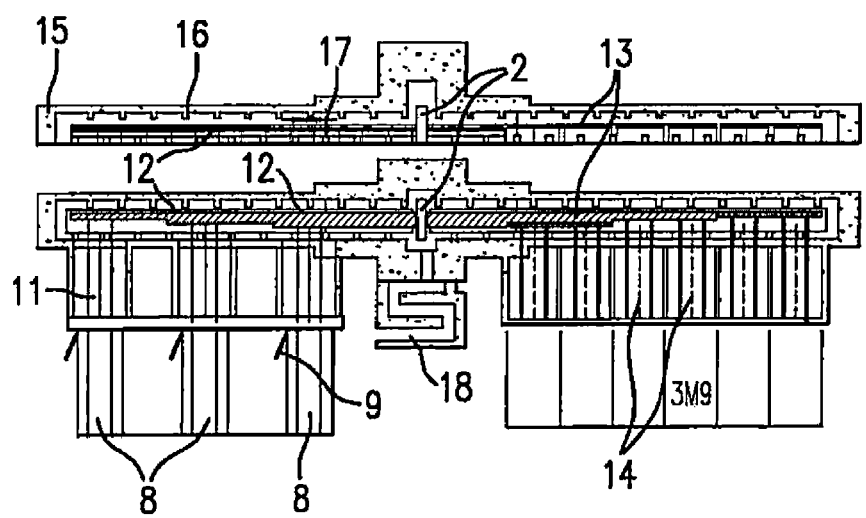
FIG. 6 is an illustration showing a conveying device and its shielding structure according to an example embodiment of the present invention.

FIG. 6 is an illustration of the conveying device 5 and shielding structure 1. The conveying device 5 includes a loading device, a longitudinal conveying device, and an unloading device. The loading device serves for spreading out the stacked logs, aligning the logs and then conveying the logs to the longitudinal conveying device; the longitudinal conveying device serves for conveying the logs through the irradiation field to get irradiation as a quarantine treatment; and the unloading device serves for conveying the logs out off the processing after the irradiation.

The loading device includes the log spreading mechanism 8, the end aligning mechanism 9, the loading mechanism 10, and the lateral loading conveying mechanism 11. The longitudinal conveying device includes the longitudinal conveying mechanism 12. The unloading device includes the log throwing mechanism 13 and the lateral unloading conveying mechanism 14. The conveying direction of the logs among the lateral loading conveying mechanism 11, the longitudinal conveying mechanism 12, and the lateral unloading conveying mechanism 14 will change by 90° twice, while the lateral loading conveying mechanism 11 and the lateral unloading conveying mechanism 14 are at certain angles with respect to the horizon plane for reducing leakage of the radiation.

It should be noted that, the loading device and the unloading device can be mounted at the same side or different side of the longitudinal conveying device.

The longitudinal conveying mechanism 12 can be divided into two portions, between which there exits a certain spatial distance, to ensure the electron beams introduced from the accelerator 2 can irradiate the logs directly without irradiating the conveying mechanism 12.

To increase the efficiency of the irradiation and the usage of the accelerators, a set of conveying devices can be provided with a plurality of loading devices, longitudinal conveying devices, and unloading devices to make a plurality of conveying lines operate simultaneously. One longitudinal conveying device can also connect to one or more loading devices and one or more unloading devices to match the loading and unloading speeds with the longitudinal conveying speed.

The log spreading mechanism 8 spreads the logs to be irradiated on the conveying line, then the end aligning mechanism 9 conducts aligning operation, and the loading mechanism 10 loads the logs one by one into the lateral loading conveying mechanism 11, during which period the conveying direction is perpendicular to the axis of the logs. During the period of conveying the log from the lateral loading conveying mechanism 11 to the longitudinal conveying mechanism 12, the conveying direction is changed by 90° to make the conveying direction consistent with the axis of the logs. After the logs are conveyed by the longitudinal conveying mechanism 12 through the irradiation field formed by the accelerators 2 and are irradiated by the electron beams, the logs enter the log throwing mechanism 13 from the end of the longitudinal conveying mechanism 12. Then the conveying direction is changed by 90° again, and the log is conveyed out off the processing by the lateral unloading conveying mechanism 14.

Figure 7:
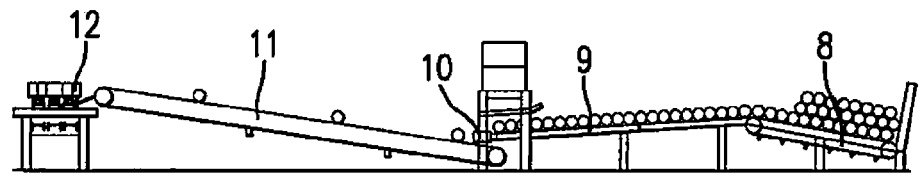
FIG. 7 is a structural illustration of a log spreading mechanism and a loading device of the conveying device according to an example embodiment of the present invention.

The structure of the loading portion is shown in FIG. 7. The loading mechanism 10 guarantees only one log will enter into the lateral loading conveying mechanism 11 at any one time. The lateral loading conveying mechanism 11 is a scraper conveyor which operates continuously. The distance between the scrapers and the operation speed are adjusted to ensure the logs can be intermittently loaded into the longitudinal conveying mechanism 12, and to ensure the time interval between the two logs entering the longitudinal conveying mechanism 12.

Figure 8:
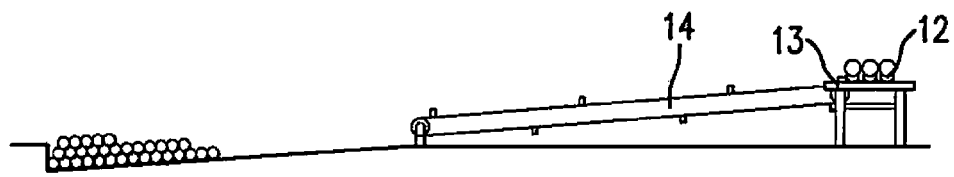
FIG. 8 is an illustration of an unloading device of the conveying device according to an example embodiment of the present invention.

The structure of the unloading portion is shown in FIG. 8. The log throwing mechanism 13 is mounted at the end of the longitudinal conveying mechanism 12, and the lateral unloading conveying mechanism 14 conveys the logs thrown by the log throwing mechanism 13 out off the conveying processing.

Figure 11:
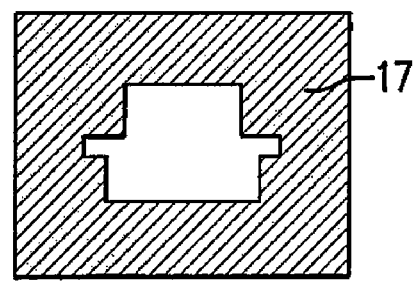
FIG. 11 is an illustration of a section of a throat plate according to an example embodiment of the present invention.
Figure 12:
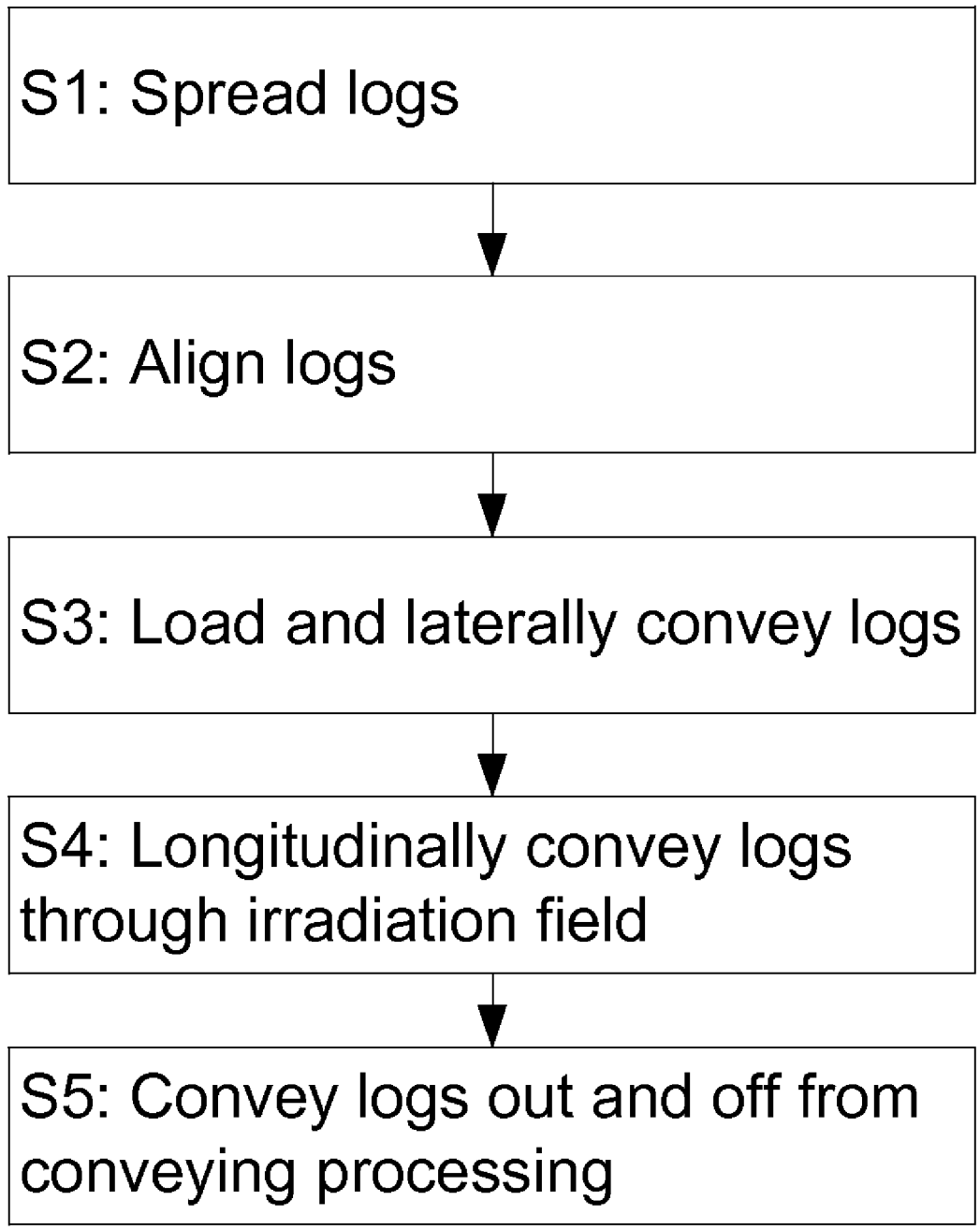
FIG. 12 is a flowchart which illustrates an irradiation method according to an example embodiment of the present invention.

During irradiation of the log as a quarantine treatment with the electron beams, the electron beam is required for high current and high energy, which results in difficulty in radiation protection, particularly when there is no shielding door. Because in the present invention the log will go through the conversion from longitudinal conveying (loading portion) to lateral conveying (irradiation section), and then to longitudinal conveying (unloading portion), the whole conveying passage is in a form of a simple maze. However, the maze in the present invention differs from the conventional maze in that a specialized shielding structure is required to meet the requirement of the radiation protection of the irradiation system as a quarantine treatment on the log with the electron beams. Therefore, when the accelerator is in operation, the leakage dose level outside the shielding structure meets the relevant requirements according to the international regulation ("International Basic Safety Standards for Protection Against Ionizing Radiation and for the Safety of Radiation Sources," IAEA, No. 115, 1996), therefore ensuring safety of operators and public Referring to FIG. 6, the shielding structure 1 according to the present invention includes shielding walls 15, throat plates 17, and a maze 18. The accelerators 2 are located at a center position of the whole shielding structure 1. The shielding walls 15 are formed along both sides and the top of the log conveying device 5. The throat plates 17 are located between a loading entrance most adjacent to the accelerator 2 and the accelerator 2, and between the accelerator 2 and an unloading exit most adjacent to the accelerator 2, for lowering the radiation level outside the loading entrance and outside the unloading exit caused by the scattered X-ray, which is the secondary radiation generated by the primary electron beams hitting on the logs and the scattered electrons hitting on the conveying device. The section view of the throat plate 17 is shown in FIG. 11.

The maze 18 is arranged at a side of the accelerator 2 as a passage for staff entering into the accelerator area. The maze 18 is provided with a safety interlock which can avoid accident caused by unintentional access of the operator.

In the preferred embodiment of the present invention, the shielding walls 15 in the irradiation passage are provided with a certain number of buttresses or barriers 16 for lowering the radiation level outside the loading entrance and outside the unloading exit caused by the scattered X-ray, which is the secondary radiation generated by the primary electron beams hitting on the logs and the scattered electrons hitting on the conveying device.

Figure 9:
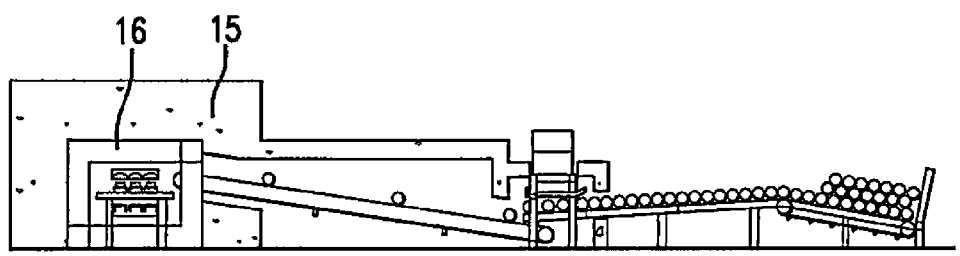
FIG. 9 is an illustration showing the radiation protection at a loading entrance according to an example embodiment of the present invention.
Figure 10:
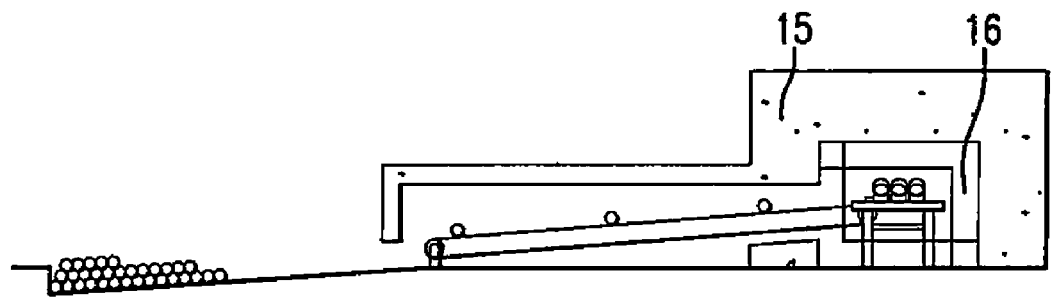
FIG. 10 is an illustration showing the radiation protection at an unloading exit according to an example embodiment of the present invention.

Furthermore, as shown in FIGS. 9 and 10, at the loading portion and the unloading portion of the present invention, the shielding doors cannot be provided due to requirement of the conveying device 5. Instead there are provided respective laser interlocks to meet the requirement on safety.

An exemplified operation process illustrated in the flowchart of FIG. 11 is described as below.

In S1, the log spreading mechanism spreads the logs carried to the location for quarantine treatment.

In S2, the end aligning mechanism aligns the logs to make the spread logs flush.

In S3, the loading mechanism loads the spread and flush logs into the lateral loading conveyor, which then conveys the logs to the longitudinal conveying mechanism.

In S4, the longitudinal conveying mechanism conveys the logs through the irradiation field formed by the accelerators, realizing the irradiation treatment by the electron beams.

In S5, the log throwing mechanism provided at the end of the longitudinal conveying mechanism throws the treated logs which are then conveyed out off the conveying processing by the unloading mechanism.

Although the present embodiment describes a method and a device for conducting irradiation treatment of the logs with the electron beams for quarantine purpose, the skilled person can realize that the present invention is applicable to other fields for solving the problems of irradiation and/or quarantine treatment of other goods. Therefore, any modification and application based on the present embodiment perceivable to the skilled person should fall into the protection scope of the present application.

What is claimed is:

1. An irradiation method, comprising:
spreading logs;
aligning the spread logs to be flush at one end;
conveying the spread and flush logs laterally along a first conveying path;
subsequently (a) passing the logs through a first throat plate arranged between an entrance to a second conveying path from the first conveying path and an arrangement of accelerators, and (b) conveying the logs longitudinally along the second conveying path and through an irradiation field formed by the accelerators, the accelerators being arranged centrosymmetrically about the second conveying path, electron beams of the accelerators subjecting the logs to a phytosanitary irradiation treatment;
passing the logs through a second throat plate arranged between the arrangement of accelerators and an exit from the second conveying path;
throwing the irradiated logs out in a lateral direction at the exit; and
subsequently laterally conveying the logs away from a path of the longitudinal conveyance.

2. The method of claim 1, wherein:
during the spreading and aligning, a conveying direction of the log is perpendicular to the axis of the log;
during the transition from the lateral conveying to the longitudinal conveying, the conveying direction of the log is changed by 90°, such that the conveying direction is consistent with the axis of the log during the longitudinal conveying; and
during the throwing and subsequent lateral conveying, the conveying direction of the log is changed again by 90°.

3. A system for conducting irradiation with electron beams as a phytosanitary treatment, comprising:
a conveying device that:
is configured to convey logs; and
includes:
a loading device;
a longitudinal conveying device; and
an unloading device;
a shielding structure surrounding the conveying device; and
a plurality of accelerators provided in a conveying path of the conveying device;
wherein:
the plurality of accelerators are arranged in centrosymmetry about the conveying path;
the shielding structure includes:
a throat plate located between an entrance at which the logs are loadable onto the conveying path and the accelerators; and
a throat plate located between the accelerators and an exit at which the logs are removed from the conveying path;
the loading device is configured to:
spread the logs;
align the logs to be flush; and
subsequently convey the logs to the longitudinal conveying device;
the longitudinal conveying device is configured to convey the logs through an irradiation field formed by the accelerators; and
the unloading device is configured to convey the irradiated logs away from a path of the conveyance by the longitudinal conveying device.

4. The system of claim 3, wherein:
the accelerators include three accelerators;
one of the three accelerators is arranged above the conveying device; and
the other two of the three accelerators are arranged below the conveying device and, respectively, at a left and a right of the conveying device.

5. A system for conducting irradiation with electron beams as a phytosanitary treatment, comprising:
a conveying device configured to convey logs;
a shielding structure surrounding the conveying device;
a plurality of accelerators provided in a conveying path of the conveying device;
wherein:
the plurality of accelerators are arranged in centrosymmetry about the conveying path; and
the shielding structure includes:
a throat plate located between an entrance at which the logs are loadable onto the conveying path and the accelerators; and
a throat plate located between the accelerators and an exit at which the logs are removed from the conveying path.

6. The system of claim 5, wherein at least one of the accelerators is arranged below the conveying device, the system further comprising:
a protective device mounted above each of one or more of the at least one accelerator arranged below the conveying device, the protective device configured to prevent damage of the respective accelerator by sundries falling from the conveying device.

7. The system of claim 3, wherein one of the accelerators is arranged above the conveying device and another of the accelerators is arranged below the conveying device.

8. The system of claim 3, wherein:
the loading device includes:
a log spreading mechanism;
an end aligning mechanism;
a loading mechanism; and
a lateral loading conveying mechanism;
the longitudinal conveying device includes a longitudinal conveying mechanism;
the unloading device includes:
a log throwing mechanism; and
a lateral unloading conveying mechanism; and
the longitudinal conveying mechanism is divided into two portions between which there is a spatial distance to ensure the electron beams emanating from the accelerators can irradiate the logs directly without irradiating the conveying mechanism.

9. The system of claim 8, wherein:
the lateral loading conveying mechanism is a scraper conveyor which operates in a continuous manner;
a distance between the scrapers of the scraper conveyor and an operation speed of the scraper conveyor are adjusted to ensure the logs can be intermittently loaded into the longitudinal conveying mechanism and to ensure a predetermined time interval between entering by an two consecutive logs into the longitudinal conveying mechanism.

10. The system of claim 8, wherein:
a direction of conveyance of the logs is changed by 90° in a switch from conveyance by the lateral loading conveying mechanism to conveyance by the longitudinal conveying mechanism;
the conveying direction is changed by 90° in a switch from conveyance by the longitudinal conveying mechanism to conveyance by the lateral unloading conveying mechanism; and
the lateral loading conveying mechanism and the lateral unloading conveying mechanism are each arranged at respective angles with respect to a horizon plane, which angled arrangements reduce leakage of radiation.

11. The system of claim 3, wherein the loading device and the unloading device are arranged at a same side of the longitudinal conveying device.

12. The system of claim 3, wherein the loading device and the unloading device are not arranged at any same side of the longitudinal conveying device.

13. The system of claim 3, wherein the conveying device includes a plurality of conveying devices, each of which includes a respective loading device, longitudinal conveying device, and unloading device, the plurality of conveying devices forming a plurality of conveying lines configured to operate simultaneously.

14. The system of claim 3, wherein:
a single longitudinal conveying device is configured to be connected to a plurality of loading devices and a plurality of unloading devices; and
a number of the plurality of loading devices and the plurality of unloading devices to which single longitudinal conveying device is connected at any one time is selected to match speeds of the loading and unloading with a speed of the longitudinal conveyance.

15. A system for conducting irradiation with electron beams as a phytosanitary treatment, comprising:
a conveying device configured to convey logs;
a shielding structure surrounding the conveying device; and
a plurality of accelerators provided in a conveying path of the conveying device;
wherein:
the plurality of accelerators are arranged in centrosymmetry about the conveying path;
the shielding structure includes:
shielding walls surrounding the conveying device;
throat plates; and
a maze structure for access by an operator and that is external to and apart from the conveying path; and
the throat plates are located between an entrance at which the logs are loaded onto the conveying path and the accelerators, and between the accelerators and an exit at which the logs are removed from the conveying path.

16. The system of claim 15, wherein the shielding walls are provided with a number of buttresses arranged to lower a radiation level at a side of the loading entrance external to the conveying path and at a side of the unloading exit caused by scattered X-ray, which is a secondary radiation generated by primary electron beams emanating from the accelerators and hitting on the logs and by scattered electrons therefrom hitting on the conveying device.

17. The system of claim 5, wherein the accelerators are staggered from each other along a direction of conveyance of the logs through an irradiation field formed by the accelerators, such that at least a portion of one of the accelerators is located upstream of another of the accelerators with respect to the direction of conveyance.

18. The system of claim 5, further comprising:
for each of at least one of the accelerators:
a scanning box mounted at an end of the accelerator; and
a deflecting magnet mounted on the scanning box at a position adjacent to an exit titanium window, the deflecting magnet configured to deflect electron beams emanating from the scanning box into parallel beams perpendicular to a plane in which the logs are conveyed during irradiation of the logs.

19. The system of claim 3, wherein the loading device is configured to separate the logs to provide each of the logs individually to the longitudinal conveying device.

20. The system of claim 15, wherein each of at least one of the shielding walls includes a plurality of projections arranged to lower a radiation level at a side of the loading entrance external to the conveying path and a plurality of projections arranged to lower a radiation level at a side of the unloading exit caused by scattered X-ray, which is a secondary radiation generated by primary electron beams emanating from the accelerators and hitting on the logs and by scattered electrons therefrom hitting on the conveying device, different ones of the plurality of projections being at different distances to the plurality of accelerators.

21. The system of claim 5, wherein the throat plates include interior cutouts corresponding to conveying device .

22. The system of claim 21, wherein the throat plates are arranged for the conveying device to pass through the interior cutouts.

23. The system of claim 5, wherein the system is arranged for receiving logs onto the conveying path upstream of the throat plate that is located between the entrance at which the logs are loadable onto the conveying path and the accelerators.

24. The system of claim 5, wherein the plurality of accelerators produce beams at an energy range of 10-14 MeV.

25. The system of claim 5, wherein the system is arranged to maintain the logs at a single orientation relative to a direction of conveyance while on the conveying path.

26. The system of claim 3, wherein the system is arranged to maintain the logs at a single orientation relative to a direction of conveyance while on the conveying path.

27. The system of claim 15, wherein the system is arranged to maintain the logs at a single orientation relative to a direction of conveyance while on the conveying path.

* * * * *